(12) United States Patent
Glauser et al.

(10) Patent No.: US 8,580,197 B2
(45) Date of Patent: Nov. 12, 2013

(54) DIRECT PIPETTING IN COMPUTER-CONTROLLED LIQUID HANDLING WORKSTATIONS

(75) Inventors: Beat Glauser, Männedorf (CH); Michael Laab, Eppstein (DE); Eskil Trollhagen, Zürich (CH)

(73) Assignee: Tecan Trading AG, Mannedorf (CH)

( * ) Notice: Subject to any disclaimer, the term of this patent is extended or adjusted under 35 U.S.C. 154(b) by 80 days.

(21) Appl. No.: 12/988,952

(22) PCT Filed: Apr. 24, 2009

(86) PCT No.: PCT/EP2009/054988
§ 371 (c)(1),
(2), (4) Date: Feb. 3, 2011

(87) PCT Pub. No.: WO2009/130318
PCT Pub. Date: Oct. 29, 2009

(65) Prior Publication Data
US 2011/0160909 A1    Jun. 30, 2011

Related U.S. Application Data

(60) Provisional application No. 61/054,668, filed on May 20, 2008.

(30) Foreign Application Priority Data

Apr. 24, 2008   (CH) ..................... 00644/08

(51) Int. Cl.
*G01N 35/10* (2006.01)
*G05B 17/00* (2006.01)

(52) U.S. Cl.
USPC .............. 422/67; 422/63; 422/64; 422/65; 422/502; 436/180; 73/864.01; 700/266; 345/619

(58) Field of Classification Search
None
See application file for complete search history.

(56) References Cited

U.S. PATENT DOCUMENTS 5,443,791 A * 8/1995 Cathcart et al. ............... 422/65
5,841,959 A   11/1998 Guiremand
(Continued)

FOREIGN PATENT DOCUMENTS

JP     9072911 A      3/1997
WO     WO 00/70490 A  11/2000

OTHER PUBLICATIONS

Written Opinion of the International Searching Authority of International Application No. PCT/EP2009.

(Continued)

*Primary Examiner* — P. Kathryn Wright
(74) *Attorney, Agent, or Firm* — Notaro, Michalos & Zaccaria P.C.

(57) ABSTRACT

In a control method for a computer-controlled liquid handling workstation with a work surface, a motorized pipetting robot with at least one pipette, and a control computer, to which the pipetting robot is connected, a control program activated in the control computer enables the pipetting robot to position the pipette at specific positions on the work surface and to execute a specific action using the pipette. The interface includes an input mechanism, visualization mechanism, interface software, and an electronic memory. The visualization mechanism visualizes the positions at which containers are situated on the work surface of the liquid handling workstation and a selection of the specific actions executable using the pipettes.

5 Claims, 3 Drawing Sheets

(56) References Cited

U.S. PATENT DOCUMENTS

| | | |
|---|---|---|
| 6,909,981 B2 | 6/2005 | Gavin et al. |
| 2004/0033164 A1 | 2/2004 | Naito |
| 2006/0048846 A1 | 3/2006 | Roenneburg |
| 2007/0077643 A1 | 4/2007 | Nakamura |
| 2008/0063570 A1 | 3/2008 | Fujino |

OTHER PUBLICATIONS

European Search Report of Application No. EP 13157364.4.

* cited by examiner

Starting main work flow:

Pipetting position work flow:

Legend:

Configure Pipette Tips:

DIRECT PIPETTING IN COMPUTER-CONTROLLED LIQUID HANDLING WORKSTATIONS

RELATED PATENT APPLICATIONS

This international patent application claims priority of the Swiss patent application No. 00644/08 of Apr. 24, 2008 and of the U.S. Provisional Application No. 61/054,668 of May 20, 2008. The entire content of these two priority applications is incorporated herein for all purposes and intents.

TECHNICAL FIELD OF THE INVENTION

The invention relates to an interface for a computer-controlled liquid handling workstation according to the preamble of independent Claim 1. Liquid handling workstations of this type comprise a work surface for the placement of containers, a motorized pipetting robot, and a control computer. This work surface is preferably oriented essentially horizontally. The pipetting robot preferably comprises at least one pipette for aspirating and dispensing liquid samples. Typically, each of these pipettes is fluidically connected via an individual line to an activatable pump, preferably to a motorized piston pump or to a micro-diaphragm pump. Usually, the control computer is electrically connected to the pipetting robot and its pumps. At least parts of a control program activated in this control computer enable the pipetting robots to position the at least one pipette at specific positions on the work surface and execute a specific action there using the at least one pipette. Typically, such specific actions are selected from a group of actions which comprise the receiving, flushing, and discarding of a pipette tip and the aspirating, mixing, and dispensing of a volume of a liquid sample.

RELATED PRIOR ART

Computer-controlled liquid handling workstations of this type are known per se and are built and sold by the current applicant under the trade name FREEDOM EVO, for example. Such more or less complex liquid handling workstations comprise a control computer, which is equipped with control software. Such control software typically offers a user a broad palette of possible applications, such as sample preparation or reagent addition, production of dilution series, enhancing density of the content of microplates having 96 wells on microplates having 384 wells, and many more. In accordance with the construction of the control software, it is expected of a user that he (preferably with the aid of an implemented user guide) establishes the detailed execution of a sequence of work steps in a so-called script. Scripts of this type may be stored in the control computer and processed using the liquid handling workstation immediately or at a later time. The control of the pipetting robot, as it is established in the control program in the control computer, is thus based on such scripts in the form of software instructions fixed in tabular form.

From US 2006/0048846 A1 an instrumentation control software is known for controlling a liquid handling instrument. In order to define a sequence of working steps to be carried out in the liquid handling instrument, the selectable means are displayed in a name list (most of the time as a pull-down menu). This software enables a user to control a liquid handling instrument via assembling a list of commands (names) in a relative extensive but rather complex way. Working with this software is further complicated by a unique non-validation mode From U.S. Pat. No. 5,841,959 a robotic interface for programming an automated liquid handling apparatus is known. In order to define a sequence of working steps to be carried out with the liquid handling apparatus, the selectable means (e.g. "aspirate", "dispense", Z-drive up/down") are displayed on a display screen as a series of icons from which a "string" of icons is to be composed. The individual icons arranged in the order of the process to be carried out. At least one of these first icons (providing a visual representation of a function of the apparatus) can be selected and expanded to show second icons that comprise the function of said at least one of the first icons, at least one of the second icons representing a sub-function of the apparatus. Also this robotic interface enables a user to control a liquid handling instrument via assembling a list of commands (icons) in a relative extensive but rather complex way, including editing the functions of the icons.

From US 2008/0063570 A1 a sample analyzer is known to include: a reagent arranging section, an analyzing section, a display device, an input device, and a display control section for displaying a reagent arrangement and indicating a plurality of reagent marks that are related to a particular reagent. By arrangement of each reagent mark on the display corresponds to arrangement of the each reagent on the reagent arranging section, the display control section displaying detailed information about the reagents that correspond to the reagent mark selected by the input device on the display device. Complex information and activities (provision of samples and reagents, mixing of samples and reagents, and analysis of these mixtures) can be monitored and controlled via a management touch screen. The touch screen in addition comprises start and stop buttons form commencement and termination of the analysis.

From WO 00/70490 A2, methods, apparatus, articles of manufacture, and user interfaces for performing automated biological assay preparation and macromolecule purification are known. Also disclosed is a graphical user interface (GUI) for preparing the assays and macromolecule purification. As demonstrated with flow charts, different sets of user specific method parameters and steps are defined and compared with each other, the sets of steps then being executed one after the other. Alternatively, a first set of user specific method parameters is created and then checked for intern incompatibility before carrying out the set of working steps. All sets comprise diverse checking and/or decision steps.

OBJECT AND SUMMARY OF THE INVENTION

The object of the present invention is to propose an interface and/or a method, using which a computer-controlled liquid handling workstation may be remotely controlled in real time and without preparing a programming script for executing simpler liquid handling actions.

This object is achieved according to a first aspect by the features of the independent Claim 1 or 2 respectively, in that two alternative versions of an interface are proposed for a computer-controlled liquid handling workstation. The workstation comprises:

(a) an essentially horizontally oriented work surface for the placement of containers;
(b) a motorized pipetting robot, having at least one pipette for aspirating and dispensing liquid samples;
(c) a control computer, to which the pipetting robot is electrically connected, at least parts of a control program activated in this control computer enabling the pipetting robot to position the at least one pipette at specific positions on the work surface and to execute a specific action there using the at least one pipette, wherein the interface is connectable to the control computer or integrated therein and comprises input means, visualization means, interface software, and an electronic memory, the visualization means at least being implemented to visualize in the form of icons the positions at which containers are situated on the work surface of the liquid handling workstation and a selection of the specific actions executable using at least one pipette, and wherein information about these pipettes and positions are storable in the electronic memory and retrievable therefrom using the interface software.

The interface for a computer-controlled liquid handling workstation according to a first and preferred alternative of the invention is characterized in that the interface and the interface software are implemented to visualize as icons at least one pipette, optionally selected by the input means or by the interface, and at least one designated pipetting position on a specific container, and in that the interface and the interface software are implemented to direct the pipetting robot of the computer-controlled liquid handling workstation to position the selected pipettes at the designated pipetting positions of the specific container immediately after designating the specific position and prior to executing the selected specific action.

The interface for a computer-controlled liquid handling workstation according to a second alternative of the invention is characterized in that the interface and the interface software are implemented to visualize as icons at least one pipette, optionally selected by the input means or by the interface, and at least one designated pipetting position on a specific container, and in that the interface and the interface software are implemented to visualize, in a 2D or 3D simulation, the pipetting robot of the computer-controlled liquid handling workstation to virtually position the selected pipettes at the designated pipetting positions of the specific container immediately after designating the specific position and prior to executing the selected specific action.

This object is achieved according to a second aspect by the features of the invention, in that two alternative versions of a method are proposed for the remote control of such a computer-controlled liquid handling workstation.

The method according to the invention defines a use of an interface for a computer-controlled liquid handling workstation, the workstation comprising:

(a) an essentially horizontally oriented work surface for the placement of containers;
(b) a motorized pipetting robot, having at least one pipette for aspirating and dispensing liquid samples;
(c) a control computer, to which the pipetting robot is electrically connected, at least parts of a control program activated in this control computer enabling the pipetting robot to position the at least one pipette at specific positions on the work surface and to execute a specific action there using the at least one pipette, wherein the interface is connected to the control computer or integrated therein and comprises input means, visualization means, interface software, and an electronic memory, the visualization means at least being implemented to visualize in the form of icons the positions at which containers are situated on the work surface of the liquid handling workstation and a selection of the specific actions executable using at least one pipette, and wherein information about these pipettes and positions are stored in the electronic memory and retrieved therefrom using the interface software.

The method according to a first and preferred alternative of the present invention is characterized in that the interface and the interface software are used to visualize as icons at least one pipette, optionally selected by the input means or by the interface, and at least one designated pipetting position on a specific container, and in that the interface and the interface software are used to direct the pipetting robot of the computer-controlled liquid handling workstation to position the selected pipettes at the designated pipetting positions of the specific container immediately after designating the specific position and prior to executing the selected specific action.

The method according to a second alternative of the present invention is characterized in that the interface and the interface software are used to visualize as icons at least one pipette, optionally selected by the input means or by the interface, and at least one designated pipetting position on a specific container, and in that the interface and the interface software are used to visualize, in a 2D or 3D simulation, the pipetting robot of the computer-controlled liquid handling workstation and to virtually position the selected pipettes at the designated pipetting positions of the specific container immediately after designating the specific position and prior to executing the selected specific action.

Additional preferred features according to the invention result from the particular dependent claims.

In the context of the present invention, the term "remote or remotely" is to be understood as "human effected input means for controlling the control computer of the liquid handling workstation. Examples of such input means are well known as e.g. a keyboard.

The term "electrically connected", which describes the connection between pipetting robot and control computer, is to be understood as "functionally connected by electrically conductive wires, wireless connections, electronic connection or by any useful connection using electromagnetic waves".

The term "control computer" is to be understood as "any digital control device" that is implemented as e.g. a microprocessor chip incorporated in the workstation, a microprocessor chip incorporated in a personal computer or other internal or external digital control equipment.

The term "fluid" is to be understood as "any non-solid material like a gas or liquid, or a gas/liquid mixture". In consequence, the term "fluidically connected" is to be understood as "connect such that a fluid may pass through the connection line".

The present invention comprises the following advantages:

A complex liquid handling workstation may be remote-controlled using a simple interface which enables intuitive operation. Specific pipettes may be selected on a touch screen using a finger or instrument by touching the icons or virtual switches and specific work may be assigned to these pipettes, upon which the interface causes the liquid handling workstation to execute this work immediately.

The immediate execution of the commands input in the interface may be visually tracked in real time on the liquid handling workstation, so that the impression arises for the user that he controls the entire liquid handling workstation using his finger or a control pen, for example.

The visualization of the pipetting robot of the computer-controlled liquid handling workstation in a 2D or 3D simulation and virtually positioning the selected pipettes at the designated pipetting positions of the specific container immediately after designating the specific position enables a user to configure specific actions and series of specific actions without the need to occupy the real robot of the liquid handling workstation. Also complete offline work and the preparation and storage of specific actions and series of specific actions with limited or even without any connection to the liquid handling workstation is possible. However, the optical control of the selected pipettes, positions and actions is only virtual.

Interactive error handling allows immediate engagement in running or triggered processes. For example, if the intended quantity of liquid cannot be aspirated from the selected container (for example, because the trough is empty), the user has the capability of inputting appropriate alternative commands. For example, an alternative trough may be activated using the pipette, in order to aspirate the necessary liquid volume therefrom. However, the empty trough may also be refilled or replaced with a full one.

BRIEF INTRODUCTION OF THE DRAWINGS

The present invention is explained in greater detail hereafter using the figures appended to this application. These figures disclose preferred embodiments of the invention without restricting its scope. In the figures.

DETAILED DESCRIPTION OF PREFERRED EMBODIMENTS

Figure 1:
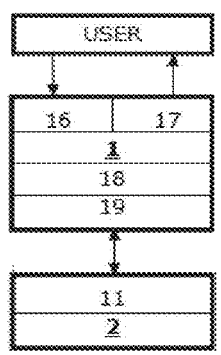
FIG. 1 shows an overview diagram of the situation of a user in relation to a liquid handling workstation with the interposed interface.

FIG. 1 shows an overview diagram of the situation of a user in relation to a liquid handling workstation with the interposed interface according to the invention. This interface 1 is capable of the remote control of a computer-controlled liquid handling workstation 2.

Figure 2:
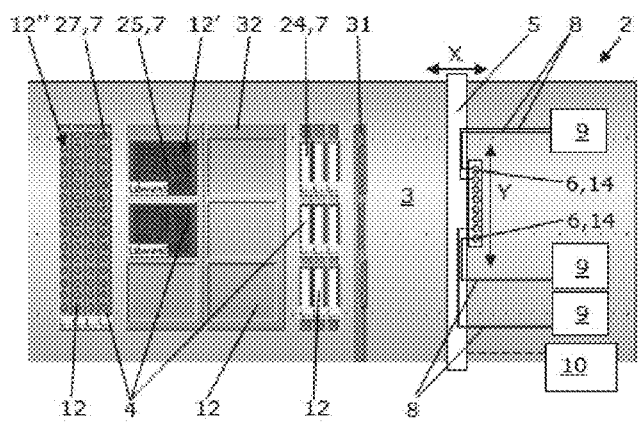
FIG. 2 shows a top view of a work surface of the liquid handling workstation having a pipetting robot, various labware (containers) being placed on the work surface.

FIG. 2 shows a top view of a work surface of a liquid handling workstation 2 having a pipetting robot 5, various containers 4 being placed on the work surface 3. A selection of preferred containers 4 such as sample tubes 27, which are preferably placed in so-called "racks" on the work surface 3 of the liquid handling workstation 2, or microplates 25 having 24, 96, 384, or 1536 wells, for example, is shown here. The preferred containers also include so-called troughs 24 and further containers 4',4" (not shown here) for at least temporarily storing liquids.

Furthermore, the workstation 2 comprises a motorized pipetting robot 5 having at least one pipette 6 for aspirating and dispensing liquid samples 7. A pipetting robot 5 is shown here, which may be moved in the longitudinal axis (X) of the liquid handling workstation 2 and which has eight pipettes 6, each having a pipette tip 14, which can be moved, in a direction (Y) perpendicular to the X axis, transversely over the work surface 3 of the liquid handling workstation 2 and may be lowered at any arbitrary location on this work surface 3.

Each pipette 6 preferably is fluidically connected via an individual line 8 to an activatable pump 9. This means that a liquid (e.g., system liquid), a gas (e.g., inert gas), or a combination of both (e.g., system liquid with air gap) is present between the conveying element of the pump and the pipette 6 and/or its pipette tip 14, using which a liquid sample 7 is to be aspirated and/or dispensed. The conveying element of the pump may be a pump piston, a diaphragm, or a combination of both. Gear wheel pumps or peristaltic pumps may also be used for conveying (aspirating and/or dispensing) liquids; in fact, the interface 1 according to the invention for a computer-controlled liquid handling workstation 2 is practically independent of the particular pump technology used for conveying liquids and/or fluids.

In addition, the liquid handling workstation 2 comprises a control computer 10, to which the pipetting robot 5 (and/or its drives, which are not shown here) and its pumps 9 (and/or their drives, which are also not shown here) are electrically connected. At least parts of a control program 11 activated in this control computer 10 enable the pipetting robot 5 to position the at least one pipette 6 at specific positions 12,12',12" on the work surface 3 and execute a specific action 13 there using the at least one pipette 6. The specific actions are known to those skilled in the art from the field of liquid handling and comprise the receiving, flushing, and/or discarding of a pipette tip 14 and the aspirating, mixing, and/or dispensing of a volume 15 of a liquid sample 7. Depending on the selected action or sequence of selected actions 13, the control program 10 enables the pipetting robot 5 to execute them. Such specific positions 12,12',12" are selected from the inside 12 of troughs 24, the wells 12' of a microplate 25, and the interior 12" of sample tubes.

The interface 1 according to the invention is preferably connected to the control computer 10. However, it may just as well be integrated in this control computer 10. The advantage of a separate interface 1 is its flexibility and mobility, which allow this interface to be used at different liquid handling workstations 2 as needed and if desired, only temporarily. The advantage of an interface 1 integrated in the control computer 10 of a specific liquid handling workstation 2 is that, for example, the interface 1 may participate in the computer performance of the control computer 10 and its peripheral devices, which are already provided.

The control computer 10 is preferably a personal computer (PC) or a processor integrated in the workstation 2. Therefore, any electronic processing unit (CPU) is understood as a control computer 10, whether it is integrated in the workstation 2 (embedded CPU) or only made available thereto.

The interface 1 according to the invention comprises (as shown in FIG. 1), input means 16, visualization means 17, interface software 18, and an electronic memory 19.

Input means 16 which are selected from a group which comprises a computer mouse 21 or a touchpad 22 are preferred. These two alternative input means are capable of moving an arrow or another indicator on a display screen and clicking on virtual switches 28,28' or so-called "icons" 35 thereon. The use of a sensor display screen 23, i.e., a so-called "touch screen", is especially preferred, because it is simultaneously used as the input means 16 (for example, by finger touch) and also as the visualization means 17. The list of the input means 16 may be lengthened arbitrarily, thus, for example, graphic tablets or joysticks may also be used for selecting and operating the visualized operating elements of the interface 1.

The visualization means 17 are at least implemented for visualizing the available pipettes 6, the positions 12,12',12", at which containers 4 are situated on the work surface 3 of the liquid handling workstation 2, and a selection of the specific actions 13 executable using the pipettes 6. In order that the necessary information about these pipettes 6 and positions 12,12',12" on the labware items may be stored in the interface 1, it comprises an electronic memory 19, from which this information is retrievable using the interface software 18 on demand.

Figure 3:
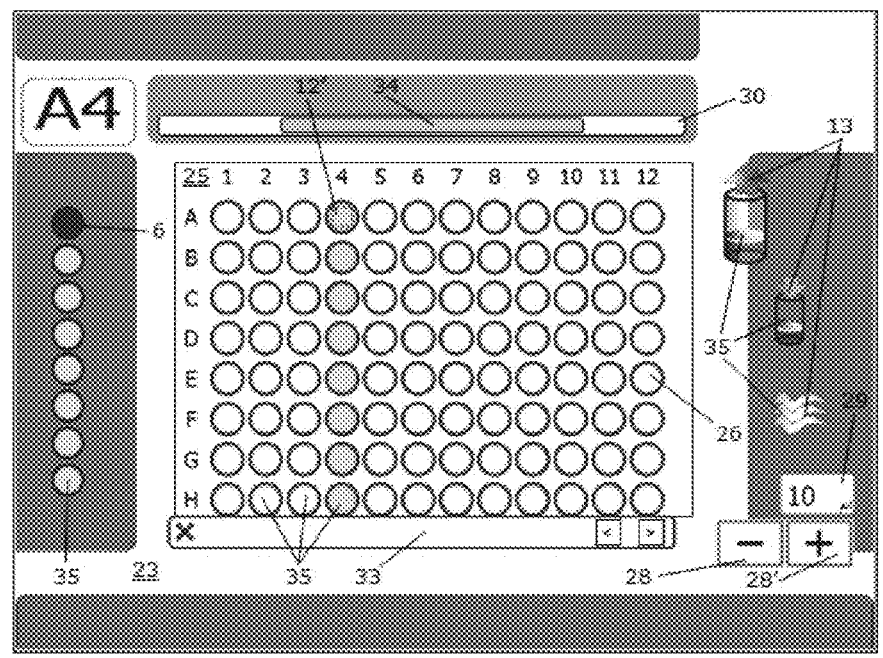
FIG. 3 shows a first screenshot of the visualization means (display screen) according to a preferred embodiment, having a selected item of labware (microplate)

FIG. 3 shows a first screenshot of preferred visualization means (sensor display screen 23) according to a preferred embodiment. The labware selected here is a microplate 25 having 96 wells 26.

The remote control of the computer-controlled liquid handling workstation 2 is performed as follows: by selecting at least one available pipette 6 and one specific action 13 and/or the position 12,12',12" of a specific container 4 or labware, which is visualized as icons 35 using the visualization means 17, using the input means 16, the interface software 18 activates the control program 11 directly so that the pipetting robot 5 positions the at least one selected pipette 6 directly at the selected position 12,12',12" on the labware and/or executes a selected specific action 13 using the selected pipette 6. Such specific positions 12,12',12" are selected from the inside 12 of troughs 24, wells 12' of a microplate 25, and the interior 12" of sample tubes.

In detail, remote-controlled liquid handling work of this type runs as follows, for example:
1. The uppermost pipette 6 (the rearmost on the work surface 3 of the liquid handling workstation 2) has been selected on the screenshot in FIG. 3 (see left side of FIG. 3). This was performed here by tapping the pipette 6 using a finger or tool (operating stylus), as such tools are known from working with a graphic user interface (a so-called "GUI"). Alternatively, this pipette 6 may be selected by clicking using a mouse or selection using a touchpad. The corresponding field on the display screen preferably changes color, as shown. In addition, and immediately after clicking, the selected pipette or pipettes are moved down by the pipetting robot 5 for some time and distance to enable the operator to optically confirm his selection of pipettes 6.
2. As the special action 13, the user has selected the option "aspiration", upon which the corresponding icon 35 has been shown larger and brought forward at least partially from the gray option field (see right side of FIG. 3).
3. By actuating the virtual switches 28,28', the user has set the desired volume to 10 µl, as is visible on the volume display 29.
4. The user has then also determined the target of the action, the well A/4, by tapping, upon which the pipetting robot 5 has immediately positioned the rearmost pipette 6 above the well A/4 (emphasized here by a dashed square) of this microplate 25. The position selected for the pipette 6 (for example, top left on the display screen) is displayed simultaneously. Further options (not selected here) comprise dispensing a liquid sample 7 (icon 35 having arrow directed into the container) and washing the pipette tip (icon 35 identified by three waves).
5. To start a pipetting or dispensing process, the user must hold a finger, tool, or another display and/or input device for a certain time on the selected process sign or the container selection (well A/4 here). This has the advantage that only intentionally triggered processes are executed, and, for example, unintentional tapping of an icon 35 still cannot trigger a process. Moreover, an additional actuation button is not necessary and beeping signals (which may annoy coworkers) for acknowledging commands may be dispensed with.

A dwell or activation time of approximately 5 to 10 seconds is preferred; however, this time may also be lengthened or shortened. The status display 30 preferably comprises a status bar 34 having a first function: the passage of the dwell or activation time is displayed, so that the status bar 34 of this status display 30 fills up completely upon the passage of the dwell or activation time. The successful ending of a specific action 13 is again displayed by the status bar 34, which preferably assumes a green color in the event of a positive result or a red color in the event of a negative result.

Preferably, at least one virtual switch 28,28' for increasing or reducing the volume 15 of a liquid sample 7 is visualized using the visualization means 17. The currently selected volume 15 is preferably made visible in a volume display 29. Using the visualization means 17 a labware selection display 33 is preferably also made visible. Such a preferred labware selection display 33 comprises a virtual X button for changing over the visualized view. For example, by clicking or tapping the X button, a changeover is made to the display screen according to FIG. 4. Additional display screen representations may also be selected, such as the selection of various disposable pipette tips, so-called "disposable tips" (not shown). Such a preferred labware selection display 33 preferably also comprises a forward button (>) and a back button (<), so that the individual types of containers 4 or "labware", which are present on the work surface 3 of the liquid handling workstation 2 and are stored in the electronic memory 19, may be selected using scrolling.

In order to discuss the just described working steps in more detail and to demonstrate ease and flexibility of working with the interface according to the invention, flow charts are added to the application.

Figure 4:
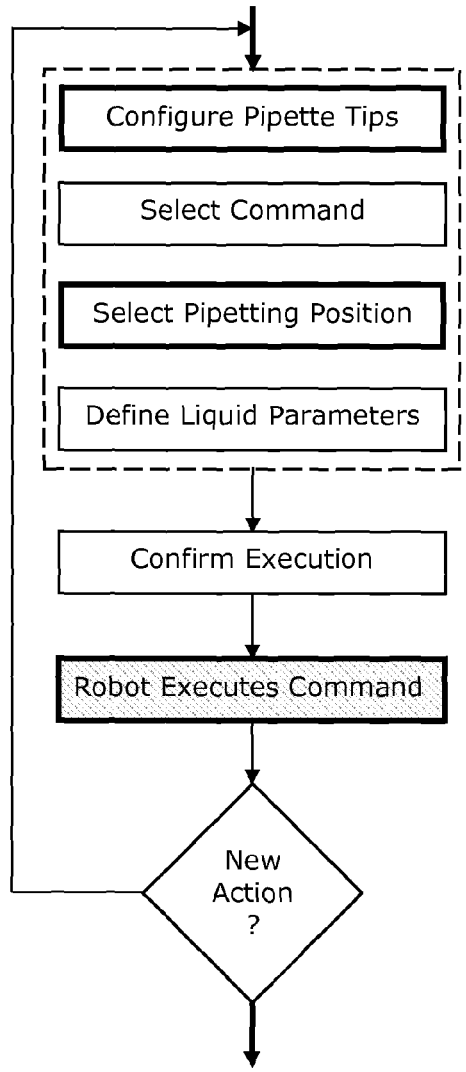
FIG. 4 shows a flow chart of a main working level with optional actions and optional sequences of actions.
Figure 6:
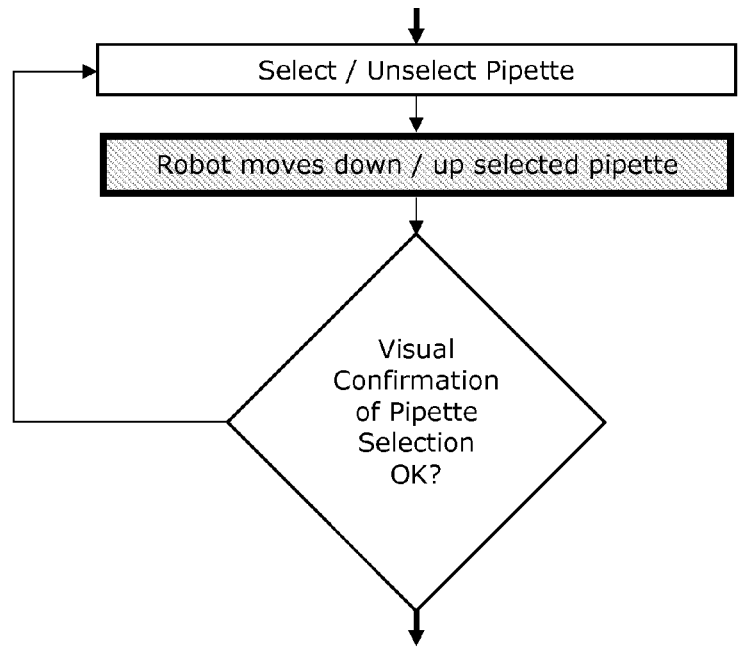
FIG. 6 shows the configuration of pipette tips in a second flow chart of a second working level with fixed sequence of actions.

FIG. 4 shows a flow chart of a main working level with optional actions and optional sequences of actions. This main work flow chart is a representation of four first level actions, which consist (in the sequence as shown) of:

Pipette Configuration this is an optional action in order to define the pipette 6 (or the pipettes 6) that is (are) selected for carrying out intended specific actions (details see FIG. 6). Immediately after defining, the selected pipette or pipettes 6 are moved down by the pipetting robot 5 for some time and distance to enable the operator to optically confirm his pipette configuration.

Alternatively, the interface 1 automatically defines a pipette configuration according to a requested specific action or sequence of specific actions and according to a number of defined specific positions 12,12',12".

Select Command this is a mandatory action in order to select specific actions from e.g. aspirate, dispense, mix.

Figure 5:
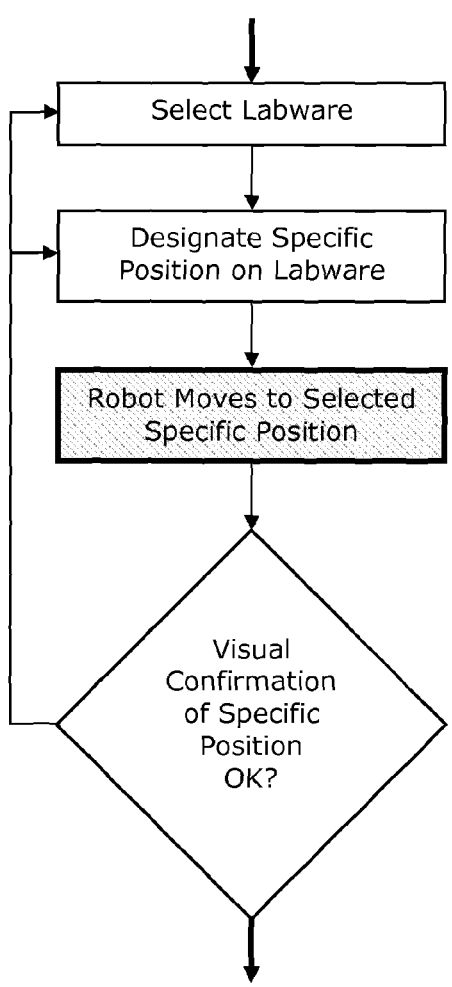
FIG. 5 shows the selection of a pipetting position in a first flow chart of a second working level with a fixed sequence of actions.
Figure 5:
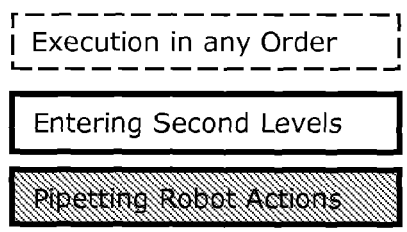
Figure 5:
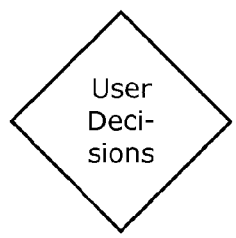

Select Pipetting Position this is a mandatory action in order to define the specific positions 12,12',12" where a specific action has to be carried out (see FIG. 5).

Define Liquid Parameters this is an optional action, because the required liquid parameters may be already defined (if not, the user can define the volume as shown already, the liquid class of the sample to be pipetted etc.).

It is important to point out that the actual sequence of selecting these four actions is not important as the software automatically collects the requested activations of actions. Thus, the user can execute the activation of these for actions in the order he likes best. In any case, the operator has to select a pipetting position, because the liquid handling instrument is to be instructed where the user demands it to carry out a certain action.

The FIG. 5 shows the selection of a pipetting position in a flow chart of a second working level with a fixed sequence of actions:
1. The labware (e.g. a microplate 25 with 24, 96, or 384 wells) is selected. This selection can address one single labware or a number of labware according to the desired liquid handling process.
2. The specific position 12,12',12" (the well 26) where the action has to be carried out with respect to the chosen labware is to be designated. This designation can address one single well or a number of wells according to the desired liquid handling process and according to the selected pipette configuration. Such specific positions 12,12',12" are selected from the inside 12 of troughs 24, wells 12' of a microplate 25, and the interior 12" of sample tubes.
3. As soon as the labware is selected and the position in that labware is designated, the liquid handling or pipetting robot 5 instantly moves the selected pipette tip 14 to the designated specific position 12,12',12" on the labware. This allows a user controlling immediately and optically, whether the liquid handling robot 5 effectively will carry out the requested action at the right place. This unique feature gives the user the impression that he directs the liquid handling robot e.g. with a movement of his finger tip.

After selecting the correct pipettes, actions and parameters, the user must activate the selected process sign, the selected container 4 (or an additional confirmation key) for a certain dwell or activation time in order to avoid carrying out unintentional operations (see point 5 above). The user thus is carrying out the next step "Confirm Execution" as a mandatory action (see FIG. 4). The liquid handling or pipetting robot 5 then (immediately after completion of the dwell or activation time) executes the command (see last step in FIG. 4). After completion of the command, a new action can be selected according to the same or a similar scheme.

FIG. 6 shows the configuration of pipettes 6 in a second flow chart of a second working level with fixed sequence of actions:
1. One or more pipettes 6 are selected according to the desired liquid handling process by using the input means 16.
   Alternatively, the interface 1 automatically defines a pipette selection according to a requested specific action or sequence of specific actions and according to a number of defined specific positions 12,12',12".
2. Upon defining the pipette configuration, the selected pipette or pipettes 6 are immediately moved down and up by the pipetting robot 5 for some time and distance to enable the operator to optically confirm his pipette configuration. This unique feature gives the user the impression that he directs the liquid handling robot e.g. with a movement of his finger tip.

In the case no pipette tip 14 is mounted on the pipettes 6 of the liquid handling robot 5, a selected pipette 6 with its empty cone for taking up a pipette tip 14 is moved to the designated position 12,12',12" on the labware instead. The user then will recognize that a pipette tip 14 is to be mounted (or to be replaced in case the liquid handling or pipetting robot 5 is carrying a wrong pipette tip 14). The selection can comprise antecedent disposal of an already mounted pipette tip 14. As soon as the pipette tip 14 is selected, the liquid handling robot 5 instantly moves its respective pipette cone to the selected pipette tip 14. This allows a user controlling immediately and optically, whether the liquid handling or pipetting robot 5 effectively will pick up the requested pipette tip. This unique feature gives the user the impression that he directs the liquid handling robot e.g. with a movement of his finger tip.

After selecting the correct actions, parameters, and pipette tips, the user must activate the selected process sign, the selected container (or an additional confirmation key) for a certain dwell or activation time in order to avoid carrying out unintentional operations (see point 5 above). The user thus is carrying out the next step "Confirm Execution" as a mandatory action (see FIG. 4). The liquid handling robot 5 then (immediately after completion of the dwell or activation time) executes the command (see last step in FIG. 4). After completion of the command, a new action can be selected according to the same or a similar scheme.

Figure 7:
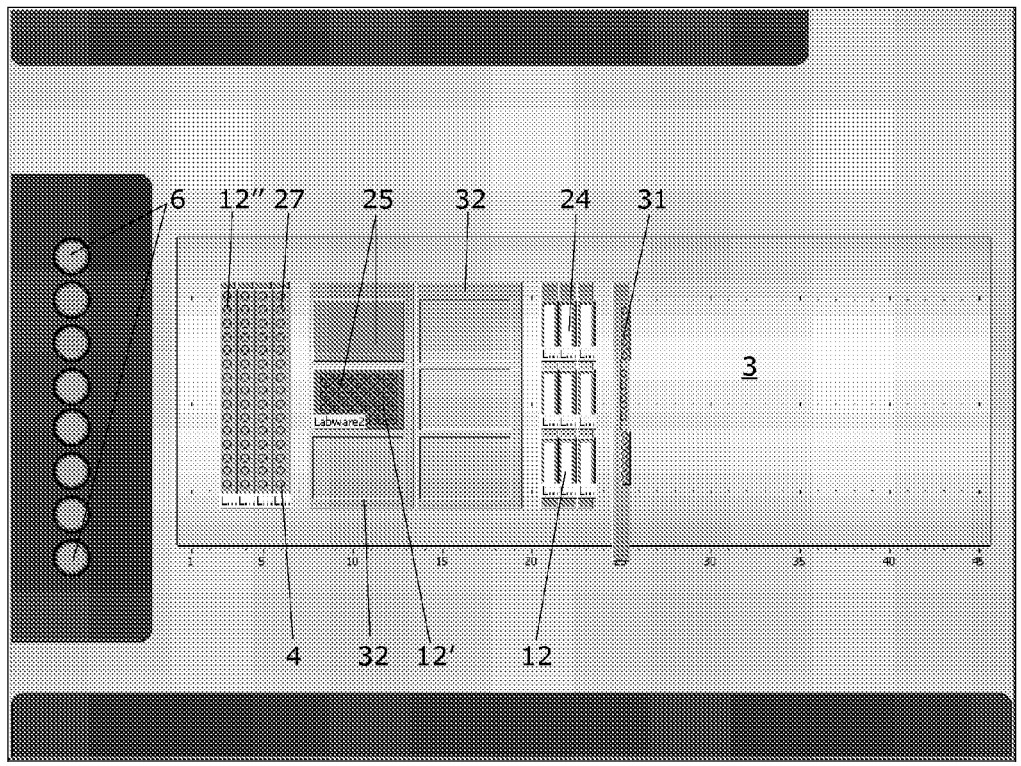
FIG. 7 shows a second screenshot of the visualization means (display screen) according to a preferred embodiment, having the layout of the work surface of the liquid handling workstation.

FIG. 7 shows a second screenshot of the visualization means 17 (display screen) according to a preferred embodiment, having the layout of the work surface of the liquid handling workstation. As already described, the visualization means 17 may be a graphic user interface (GUI), an image projecting instrument, or a display screen 20, on which the available pipettes 6, the positions 12 at which containers 4 are situated on the work surface 3 of the liquid handling workstation 2, and a selection of the specific actions 13 executable using the pipette 6 are graphically displayed as icons 35 and are selectable using the input means 16. All types of display screens come into consideration, such as computer display screens, television display screens, and other monitors. A so-called "video projector" or projector may be used as the image-projecting instrument. The image for the visualization may be projected on a wall, a screen, or also in or on the retina (e.g., projector spectacles) of the observer. Two carriers 32, which are implemented in this case for carrying three microplates, are also shown. In addition, a washing station 31 is shown, in which the pipette tips may be flushed using one or more washing liquids.

The input means 16 are especially preferably a display screen 23, on which the available pipettes 6, the positions 12 at which containers 4 are situated on the work surface 3 of the liquid handling workstation 2, and a selection of the specific actions 13 executable using the pipettes 6 are graphically represented as icons 35 and selectable by finger touch.

As shown in FIG. 3, at least one container 4 may be visualized using the visualization means 17, the container being selected from a group of containers which comprises at least one trough 24, at least one microplate 25 having a number of wells 26, or at least one sample tube 27. Tapping or clicking a container 4 which is made visible using the visualization means 17 causes its selection and simultaneously a changeover to the display according to FIG. 3. Preferably, at least one status display 30 is visualized using the visualization means 17, which displays the passage of a waiting and/or activation time or the quality of the currently executed work of a specific action 13.

A preferred method for the remote control of a computer-controlled liquid handling workstation 2 is characterized in that the information about the available pipettes 6 and the positions 12 of the containers 4 on the work surface 3 of the liquid handling workstation 2 is visually acquired by a user and manually stored in the electronic memory 19.

A particularly preferred method for the remote control of a computer-controlled liquid handling workstation 2 is characterized in that the information about the available pipettes 6 and the positions 12 of the containers 4 on the work surface 3 of the liquid handling workstation 2 are automatically recognized by the control computer 10 and stored in the electronic memory 19 of the interface 1. The automatic recognition of the available pipettes 6, in particular the pipette tips used, such as steel or plastic needles, disposable pipette tips having various equipment (e.g., filters) and/or volumes, is preferably made available to the interface 1, for example, by a liquid level detection installed in the pipetting robot 5 and may be transmitted easily to the electronic memory 19 of the interface 1, for example. The automatic recognition of the positions 12 of the containers 4 and their type (such as sample tubes 27, microplates 25, troughs 24, and the like) on the work surface 3 of the liquid handling workstation 2 is preferably executed with the aid of RFID (radio frequency identification) technology, each container 4 preferably being equipped with a so-called RFID label or a "RFID tag". The application of barcodes also allows the identification of container types and the establishment of their positions. As an alternative to the purely visual acquisition of the container types, pipette types, and their positions, a camera (e.g., a video camera) may also be used for this purpose, whose data are provided to the computer for processing via suitable software.

A sequence of specific actions 13 which has just been executed is preferably stored in electronic memory 19, so that this sequence may be retrieved at a later time from this memory 19 as an identical sequence of specific actions 13 and automatically executed once or also multiple times.

The interface 1 according to the invention allows an intuitive, interactive selection of the commands, containers, and individual actions. Individual actions may be assembled iteratively into series or sequences of actions, so that complex processing sequences may be performed, as are needed, for example, during repipetting, production of dilution series, and concentration of the content of microplates having 96 wells to microplates having 384 wells. The selected control commands for single actions, but also for entire processing sequences, are preferably stored in the electronic memory and may be retrieved as needed and, as a result, processed once or multiple times (preferably automatically).

The reference numerals in the figures each indicate identical elements, even if they are not described in detail in each case.

LIST OF REFERENCE NUMERALS 1 interface
2 liquid handling workstation
3 work surface
4,4',4" container
5 pipetting robot
6 pipette
7 liquid samples
8 individual line
9 activatable pump
10 control computer
11 control program
12,12',12" positions
13 specific action
14 pipette tip
15 volume
16 input means
17 visualization means
18 interface software
19 electronic memory
20 display screen
21 computer mouse
22 touchpad
23 sensor display screen
24 trough
25 microplate
26 well
27 sample tube
28,28' virtual switch
29 volume display
30 status display
31 washing station
32 carrier
33 labware selection display
34 status bar
35 icon

The invention claimed is:

1. A control method for a computer-controlled liquid handling workstation (2), the method comprising the following sequence of steps:
   i) providing a computer-controlled liquid handling workstation (2) comprising:
      (a) an essentially horizontally oriented work surface (3) for the placement of containers (4);
      (b) a motorized pipetting robot (5), having at least two pipettes (6) for aspirating and dispensing liquid volumes;
      (c) a control computer (10), to which the pipetting robot (5) is electrically connected, at least parts of a control program (11) activated in this control computer (10) enabling the pipetting robot (5) to position at least one of the pipettes (6) at specific positions (12,12',12") with respect to the work surface (3) and to execute a specific action there using at least one of the pipettes (6); and
      (d) an interface (1), which is connectable to the control computer (10) or integrated therein and which comprises input means (16), and visualization means (17);
   ii) visualizing as icons the at least two pipettes (6), at least one specific position (12,12',12") at which at least one container or labware is situated (4) on the work surface (3) of the liquid handling workstation (2), and at least one action executable using at least one of the pipettes (6) from a group of actions comprising receiving, flushing, or discarding a pipette tip (14), aspirating, mixing, and dispensing of a volume (15) of a liquid sample (7), using the visualization means (17);
   iii) selecting at least one pipette (6) using the input means (16), thereby defining a pipette configuration;
   iv) moving down and up the at least one selected pipette (6) immediately after defining the pipette configuration in step iii), using the pipetting robot (5), this movement of the at least one selected pipette (6) enabling the operator to confirm the defined pipette configuration;
   v) designating at least one specific position (12,12',12") of at least one container or labware, visualized in step ii), where the at least one selected pipette (6) is to execute at least one action visualized in step ii), using the input means (16);
   vi) moving the at least one selected pipette (6) to the designated specific position (12,12',12") immediately after designating said position in step v), using the pipetting robot (5), this movement of the at least one selected pipette (6) using the pipetting robot (5) of the computer-controlled liquid handling workstation (2) enabling the operator to confirm the designation of step v);
   vii) selecting at least one of the actions visualized in step ii) using the input means (16); and
   viii) executing the at least one action selected in step vii) using the at least one selected pipette (6) which has been moved to the designated specific position (12,12',12") in step vi), wherein
the movement of the at least one selected pipette in step iv) and step vi) is carried out prior to the selecting at least one of the actions of step vii) and the executing the at least one action of step viii).

2. The control method according to claim 1, further comprising the step of:
using a graphic user interface (GUI), an image-projecting instrument, or a display screen (20) as the visualization means (17).

3. The control method according to claim 1, further comprising the step of:
selecting the input means (16) from a group which comprises a computer mouse (21), a touchpad (22), a graphic tablet, a joystick, and a sensor display screen (23).

4. The control method according to claim 1, further comprising the step of:
selecting at least one container (4) from a group of containers which comprises at least one trough (24), at least one microplate (25) having a number of wells (26), and at least one sample tube (27) or any combination thereof.

5. The control method according to claim 1, wherein the at least one designated position (12,12',12") on a visualized container (4) or labware visualized in step ii) and selected in step iv) is visualized using the interface (1).

* * * * *